(12) United States Patent
Haverkost et al.

(10) Patent No.: US 10,828,090 B2
(45) Date of Patent: Nov. 10, 2020

(54) MEDICAL DEVICES WITH FLEXIBLE CIRCUIT ASSEMBLIES

(71) Applicant: Boston Scientific Scimed, Inc., Maple Grove, MN (US)

(72) Inventors: Patrick A. Haverkost, Brooklyn Center, MN (US); Martin R. Willard, Burnsville, MN (US); Derek C. Sutermeister, Ham Lake, MN (US); Joel N. Groff, Delano, MN (US); Jeffrey S. Lindquist, Maple Grove, MN (US); Robert N. Squire, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 401 days.

(21) Appl. No.: 14/593,485

(22) Filed: Jan. 9, 2015

(65) Prior Publication Data

US 2015/0196354 A1 Jul. 16, 2015

Related U.S. Application Data

(60) Provisional application No. 61/926,082, filed on Jan. 10, 2014.

(51) Int. Cl.
*A61B 18/14* (2006.01)
*A61F 7/12* (2006.01)
(Continued)

(52) U.S. Cl.
CPC .......... *A61B 18/1492* (2013.01); *A61F 7/007* (2013.01); *A61F 7/123* (2013.01);
(Continued)

(58) Field of Classification Search
CPC ........ A61B 18/1492; A61B 2018/0016; A61B 2018/0022; A61B 2018/00404;
(Continued)

(56) References Cited

U.S. PATENT DOCUMENTS 5,156,151 A 10/1992 Imran
5,238,004 A 8/1993 Sahatjian et al.
(Continued)

FOREIGN PATENT DOCUMENTS

WO 2008049087 A2 4/2008
WO 2010056771 A 5/2010
(Continued)

*Primary Examiner* — Daniel W Fowler
*Assistant Examiner* — Tigist S Demie

(57) ABSTRACT

Medical devices for sympathetic nerve modulation are disclosed. An example medical device for sympathetic nerve modulation may include a catheter shaft having a distal region. An expandable member may be coupled to the distal region. A flexible circuit assembly may be attached to the expandable member. The flexible circuit assembly may include a first electrode strip, a second electrode strip, and a sensor strip disposed between the first electrode strip and the second electrode strip. The first electrode strip may include a first electrode. The second electrode strip may include a second electrode. The first electrode and the second electrode may define a pair of bipolar electrodes.

20 Claims, 18 Drawing Sheets

(51) Int. Cl.
*A61F 7/00* (2006.01)
*H05K 1/02* (2006.01)
*A61B 18/00* (2006.01)

(52) U.S. Cl.
CPC ...... *H05K 1/028* (2013.01); *A61B 2018/0016* (2013.01); *A61B 2018/0022* (2013.01); *A61B 2018/00404* (2013.01); *A61B 2018/00434* (2013.01); *A61B 2018/00511* (2013.01); *A61B 2018/00577* (2013.01); *A61B 2018/00797* (2013.01); *A61B 2018/00815* (2013.01); *A61B 2018/1465* (2013.01); *A61B 2018/1467* (2013.01); *A61B 2018/1475* (2013.01); *A61F 2007/126* (2013.01)

(58) Field of Classification Search
CPC ........... A61B 2018/00434; A61B 2018/00511; A61B 2018/00577; A61B 2018/00797; A61B 2018/00815; A61B 2018/1465; A61B 2018/1467; A61B 2018/1475; A61F 7/007; A61F 7/123; A61F 2007/126; H05K 1/028
USPC .......................................................... 606/41
See application file for complete search history.

(56) References Cited

U.S. PATENT DOCUMENTS

| 6,508,803 | B1 | 1/2003 | Horikawa et al. | |
|---|---|---|---|---|
| 7,089,063 | B2 | 8/2006 | Lesh et al. | |
| 8,295,902 | B2 | 10/2012 | Salahieh et al. | |
| 2007/0244501 | A1 | 10/2007 | Horn et al. | |
| 2008/0188912 | A1* | 8/2008 | Stone | A61B 18/1492 607/99 |
| 2010/0204560 | A1* | 8/2010 | Salahieh | A61B 5/01 600/373 |
| 2012/0071870 | A1* | 3/2012 | Salahieh | A61B 5/01 606/33 |
| 2013/0165916 | A1 | 6/2013 | Mathur et al. | |
| 2013/0165990 | A1* | 6/2013 | Mathur | A61B 18/18 607/44 |

FOREIGN PATENT DOCUMENTS

| WO | 2011143468 | | 11/2011 |
|---|---|---|---|
| WO | 2013096916 | | 6/2013 |
| WO | 2014205388 | A1 | 12/2014 |
| WO | 2015010074 | A1 | 1/2015 |
| WO | 2015013301 | A1 | 1/2015 |
| WO | 2015038947 | A1 | 3/2015 |

\* cited by examiner

US 10,828,090 B2

MEDICAL DEVICES WITH FLEXIBLE CIRCUIT ASSEMBLIES

CROSS-REFERENCE TO RELATED APPLICATIONS

This application claims priority under 35 U.S.C. §119 to U.S. Provisional Application Ser. No. 61/926,082, filed Jan. 10, 2014, the entirety of which is incorporated herein by reference.

TECHNICAL FIELD

The present disclosure pertains to medical devices, and methods for using and manufacturing medical devices. More particularly, the present disclosure pertains to medical devices and methods that relate to sympathetic nerve modulation.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device for sympathetic nerve modulation may include a catheter shaft having a distal region. An expandable member may be coupled to the distal region. A flexible circuit assembly may be attached to the expandable member. The flexible circuit assembly may include a first electrode strip, a second electrode strip, and a sensor strip disposed between the first electrode strip and the second electrode strip. The first electrode strip may include a first electrode. The second electrode strip may include a second electrode. The first electrode and the second electrode may define a pair of bipolar electrodes.

Another example medical device for sympathetic nerve modulation may include a catheter shaft having a distal section. A balloon may be coupled to the distal section. The medical device may also include a flexible circuit assembly. The flexible circuit assembly may include a polymer substrate with a proximal region coupled to the catheter shaft and a distal region coupled to the balloon. The distal region of the polymer substrate may include a first electrode strip, a second electrode strip, and a sensor strip disposed between the first electrode strip and the second electrode strip. The first electrode strip may include one or more electrodes. The second electrode strip may also include one or more electrodes. A pair of bipolar electrodes may be defined by the one or more electrodes of the first electrode strip and the one or more electrodes of the second electrode strip.

An example method for modulating sympathetic nerves may include providing a sympathetic nerve modulation device. The sympathetic nerve modulation device may include a catheter shaft having a distal section, a balloon coupled to the distal section, and a flexible circuit assembly. The flexible circuit assembly may include a polymer substrate with a proximal region coupled to the catheter shaft and a distal region coupled to the balloon. The polymer substrate may include a first electrode strip, a second electrode strip, and a sensor strip disposed between the first electrode strip and the second electrode strip. The first electrode strip may include one or more electrodes. The second electrode strip may also include one or more electrodes. A pair of bipolar electrodes may be defined by the one or more electrodes of the first electrode strip and the one or more electrodes of the second electrode strip. The method may additionally include advancing the sympathetic nerve modulation device through a blood vessel to a position within a renal artery, expanding the balloon, and activating the pair of bipolar electrodes.

Another example medical device for sympathetic nerve modulation may include a catheter shaft having a longitudinal axis. A balloon may be coupled to the catheter shaft. A flexible circuit assembly may be coupled to the catheter shaft. The flexible circuit assembly may include two or more flexible strips. Each of the two or more flexible strips may include one or more electrodes. At least a portion of the flexible circuit assembly may be canted relative to the longitudinal axis of the catheter shaft.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
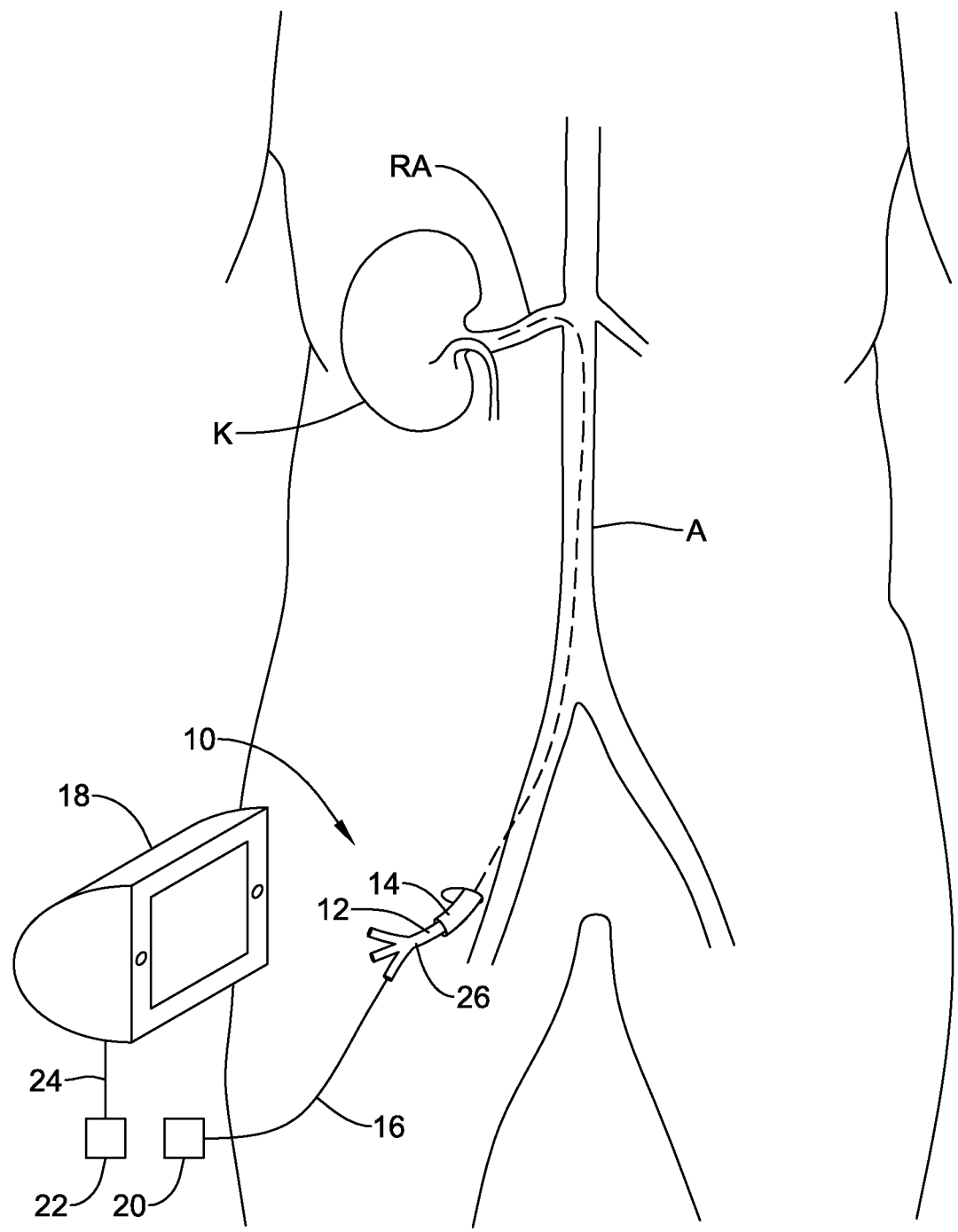
FIG. 1 is a schematic view of an example sympathetic nerve modulation system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Certain treatments are aimed at the temporary or permanent interruption or modification of select nerve function. In some embodiments, the nerves may be sympathetic nerves. One example treatment is renal nerve ablation, which is sometimes used to treat conditions such as or related to hypertension, congestive heart failure, diabetes, or other conditions impacted by high blood pressure or salt retention. The kidneys produce a sympathetic response, which may increase the undesired retention of water and/or sodium. The result of the sympathetic response, for example, may be an increase in blood pressure. Ablating some of the nerves running to the kidneys (e.g., disposed adjacent to or otherwise along the renal arteries) may reduce or eliminate this sympathetic response, which may provide a corresponding reduction in the associated undesired symptoms (e.g., a reduction in blood pressure).

Some embodiments of the present disclosure relate to a power generating and control apparatus, often for the treatment of targeted tissue in order to achieve a therapeutic effect. In some embodiments, the target tissue is tissue containing or adjacent to nerves. In other embodiments, the target tissue is sympathetic nerves, including, for example, sympathetic nerves disposed adjacent to blood vessels. In still other embodiments the target tissue is luminal tissue, which may further comprise diseased tissue such as that found in arterial disease.

Many of the devices and methods described herein are discussed relative to renal nerve ablation and/or modulation. However, it is contemplated that the devices and methods may be used in other treatment locations and/or applications where sympathetic nerve modulation and/or other tissue modulation including heating, activation, blocking, disrupting, or ablation are desired, such as, but not limited to: blood vessels, urinary vessels, other body lumens or openings, or in other tissues via trocar and cannula access. For example, the devices and methods described herein can be applied to hyperplastic tissue ablation, cardiac ablation, pain management, pulmonary vein isolation, pulmonary vein ablation, tumor ablation, benign prostatic hyperplasia therapy, nerve excitation or blocking or ablation, modulation of muscle activity, hyperthermia or other warming of tissues, etc.

FIG. 1 is a schematic view of an example sympathetic nerve ablation system 10. System 10 may include a sympathetic nerve modulation and/or ablation device 12. Sympathetic nerve ablation device 12 may be used to ablate nerves (e.g., renal nerves) disposed adjacent to the kidney K (e.g., renal nerves disposed about a renal artery RA). In use, sympathetic nerve ablation device 12 may be advanced through a blood vessel such as the aorta A to a position within the renal artery RA. This may include advancing sympathetic nerve ablation device 12 through a guide sheath or catheter 14. When positioned as desired, sympathetic nerve ablation device 12 may be activated to activate one or more electrodes (not shown). This may include operatively coupling sympathetic nerve ablation device 12 to a control unit 18, which may include an RF generator, so as to supply the desired activation energy to the electrodes. For example, sympathetic nerve ablation device 12 may include a catheter shaft 26 and a wire or conductive member 16 coupled to catheter shaft 26. Conductive member 16 may include a first connector 20 that can be connected to a second connector 22 on the control unit 18 and/or a wire 24 coupled to the control unit 18. In at least some embodiments, the control unit 18 may also be utilized to supply/receive the appropriate electrical energy and/or signal to activate one or more sensors disposed at or near a distal end of sympathetic nerve ablation device 12. When suitably activated, the one or more electrodes may be capable of ablating tissue (e.g., sympathetic nerves) as described below and the one or more sensors may be used to detect desired physical and/or biological parameters.

The use of medical devices such as device 12 may include advancing device 12 to a target region (e.g., a renal artery) through guide catheter 14, advancing a distal portion of device 12 distally out from guide catheter 14 so as to expose any electrodes or other features of device 12 to the target region, and activating the electrodes. Following the activation of the electrodes, it may be desirable to withdraw device 12 back into guide catheter 14, reposition or otherwise navigate device 12 and guide catheter 14 to another suitable location (e.g., a renal artery on the other side of the patient), and repeat the modulation/ablation procedure. In instances where a device includes one or more electrode assemblies that are attached to an expandable member such as a balloon, the "withdrawing" and "repositioning" processes could expose the electrode assemblies to forces that could lead to sheering of the assemblies, delamination of the assemblies from the balloon, or other damages that may be undesirable. The devices disclosed herein are designed to reduce damage and/or delamination that could occur, for example, when withdrawing and/or repositioning medical devices.

Figure 2:
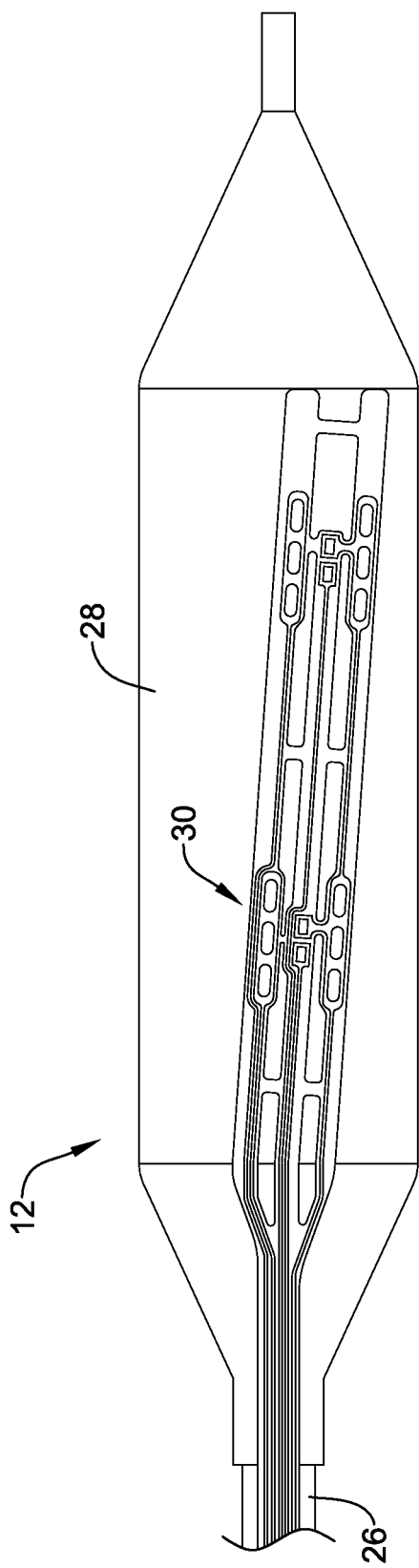
FIG. 2 is a side view of an example medical device.

FIG. 2 schematically illustrates a distal region of medical device 12. Here it can be seen that an expandable member 28 may be coupled to catheter shaft 26. In this example, expandable member 28 is a balloon. This is not intended to be limiting. Other expandable members are contemplated including expandable baskets or basket-like structures. A flexible circuit assembly 30 may be coupled to expandable member 28. Flexible circuit assembly 30 may include a number of structural features that are designed to reduce any damage, delamination, or the like that might occur when withdrawing and/or repositioning device 12. Furthermore, the configuration of assembly 30 (described in more detail herein) may allow for easier refolding of balloon 28.

Figure 3:
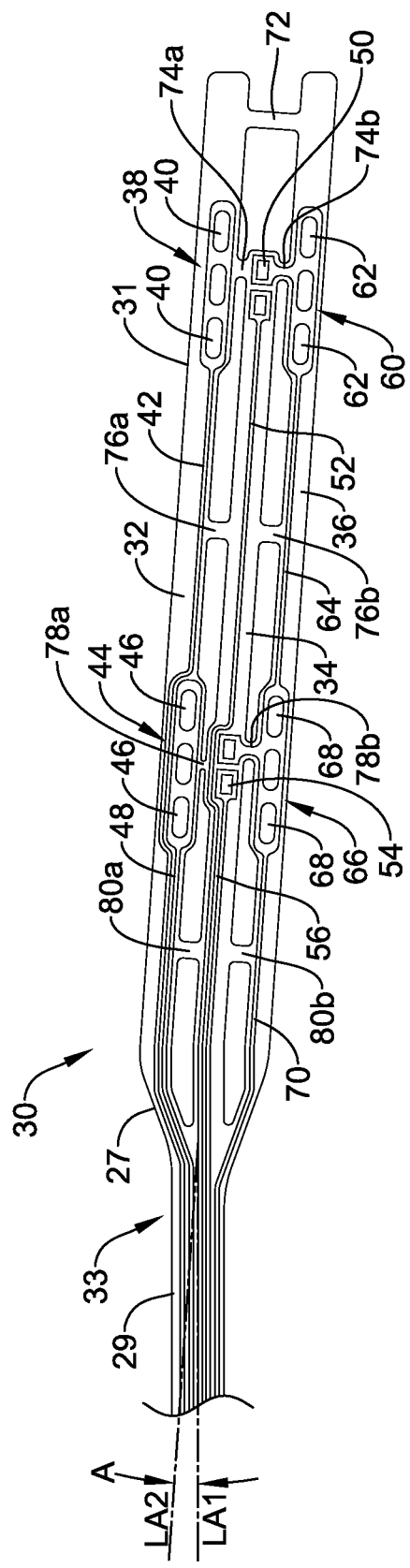
FIG. 3 is a side view of an example flexible circuit assembly.

FIG. 3 is a side view of flexible circuit assembly 30. Here it can be seen that assembly 30 may include a substrate 33 having a proximal region 29 and a distal region 31. In some embodiments, a tapered region 27 may be defined between proximal region 29 and distal region 31. Tapered region 27 may transition the width of substrate from the width along proximal region 29 to the width along distal region 31. In at least some embodiments, the overall width of substrate 33 along distal region 31 may be greater than along proximal region 29. Other configurations are contemplated.

Substrate 33 may include a first electrode strip 32, a sensor strip 34, and a second electrode strip 36. By arranging substrate into a plurality of strips 32/34/36, assembly 30 may have greater flexibility by virtue, for example, of strip 32/34/36 being able to flex or bend independently of one another. This may not only have a desirable impact on flexibility, the strip-like configuration may aid in balloon refolding. Therefore, assembly 30 may allow balloon 28 to refold into a more compact configuration when deflated. By reducing the profile of the deflated/refolded balloon 28, any damage that could be done to assembly 30 while withdrawing and/or repositioning device 12 may be reduced or otherwise eliminated.

First electrode strip 32 may include a distal electrode assembly or pad 38 having one or more electrodes 40. In this example, distal pad 38 includes three electrodes 40. Other numbers and/or configurations of electrodes 40 are contemplated. One or more leads 42 may be coupled to electrodes 40 and extend proximally therefrom. In some embodiments, first electrode strip 32 may also include one or more additional electrode assemblies such as a proximal electrode assembly or pad 44 having one or more electrodes 46. One or more leads 48 may be coupled to electrodes 46 and extend proximally therefrom. Leads 42/48, which are shown schematically, may be electrically coupled to control unit 18 so that electrodes 40/46 may be suitably energized.

Sensor strip 34 may include one or more sensors such as a sensor or sensors 50. In the drawing, two sensors 50 are shown. However, in other embodiments only one or more than two sensors may be utilized. In at least some embodiments, sensor 50 is a temperature sensor that may be disposed along a top (outward facing when in use) or bottom surface (inward facing that may be, for example, disposed along an outer surface of a balloon when in use) of sensor strip 34. For example, sensor(s) 50 may include a thermistor, thermocouple, or the like. In other embodiments, sensor(s) 50 may include another type of sensor such as a pressure sensor, force sensor, or the like. One or more leads 52 may be coupled to sensor(s) 50 and extend proximally therefrom. In some embodiments, sensor strip 34 may also include one or more additional sensors such as sensor or sensors 54. One or more leads 56 may be coupled to sensor(s) 54 and extend proximally therefrom. Leads 52/56, which are shown schematically, may be electrically coupled to control unit 18 so that sensors 50/54 may be suitably energized. In at least some embodiments, leads 52/56 may not be distinct structures and, instead, sensor(s) 50 may be electrically coupled to leads 42/48 and/or other leads disposed along substrate 33.

Second electrode strip 36 may include a distal electrode assembly or pad 60 having one or more electrodes 62. In this example, distal pad 60 includes three electrodes 62. Other numbers and/or configurations of electrodes 62 are contemplated. One or more leads 64 may be coupled to electrodes 62 and extend proximally therefrom. In some embodiments, second electrode strip 36 may also include one or more additional electrode assemblies such as a proximal electrode assembly or pad 66 having one or more electrodes 68. One or more leads 70 may be coupled to electrodes 68 and extend proximally therefrom. Leads 64/70, which are shown schematically, may be electrically coupled to control unit 18 so that electrodes 62/68 may be suitably energized.

First electrode strip 32 and second electrode strip 36 may be interconnected at a first location by a joining member 72. Joining member 72 may take the form of a portion or section of substrate 33 that extends between strips 32/36. In other embodiments joining member 72 may be a separate members that is attached to both of strips 32/36. Similarly, sensor strip 34 may be interconnected to first electrode strip 32 by a joining member 74a at a second location. Sensor strip 34 may also be interconnected to second electrode strip 36 by a joining member 74b at the second location. Strips 32/34/36 may be interconnected at a third location by one or more joining members such as joining members 76a/76b. For example, joining member 76a may extend between first electrode strip 32 and sensor strip 34. Joining member 76b may extend between sensor strip 34 and second electrode strip 36. Sensor strip 34 may be interconnected to first electrode strip 32 by a joining member 78a at a fourth location. Sensor strip 34 may also be interconnected to second electrode strip 36 by a joining member 78b at the fourth location. Strips 32/34/36 may be interconnected at a fifth location by one or more joining members such as joining members 80a/80b. For example, joining member 80a may extend between first electrode strip 32 and sensor strip 34. Joining member 80b may extend between sensor strip 34 and second electrode strip 36. The precise location of the various joining members along strips 32/34/36 may vary. Fewer or more joining members may be utilized without departing from the spirit of the disclosure.

Proximal region 29 of substrate 33 may have a longitudinal axis LA1. Distal region 31 of substrate 33 may have a longitudinal axis LA2. In at least some embodiments, the longitudinal axis LA2 of distal region 31 may be slanted or otherwise oriented at an angle A relative to the longitudinal axis LA1 of proximal region 29. This may aid in further reducing the amount of force that may be exposed to assembly 30 when, for example, withdrawing device 12 into guide catheter 14.

Figure 4:
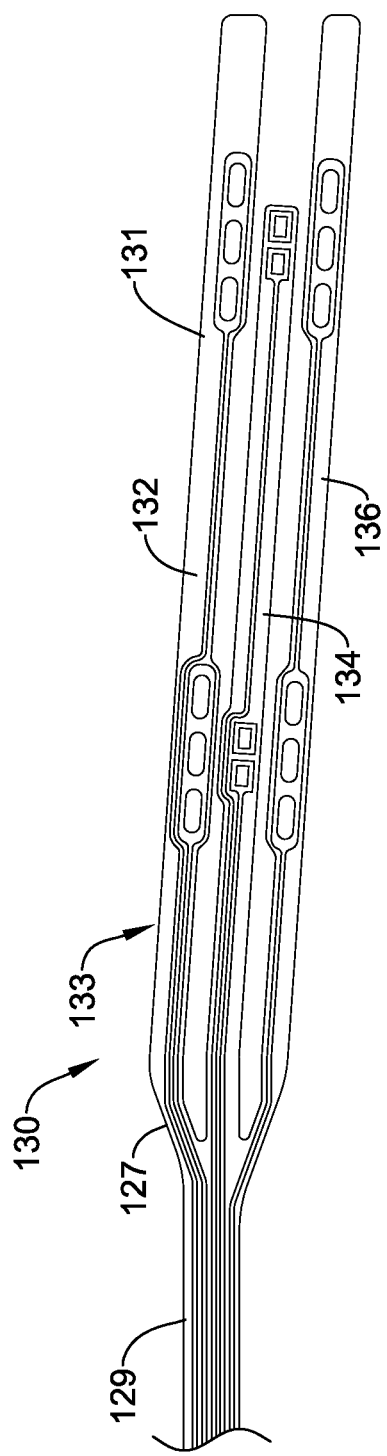
FIG. 4 is a side view of another example flexible circuit assembly.

A number of variations are contemplated for assembly 30. Some of the variations are shown in FIGS. 4-8. For example, FIG. 4 illustrates another example flexible circuit assembly 130 that may be similar in form and function to other assemblies disclosed herein. Assembly 130 may include substrate 133 having proximal region 129, distal region 131, and tapered region 127 disposed therebetween. In this example, first electrode strip 132, sensor strip 134, and second electrode strip 136 are substantially free from connection along their lengths. In other words, flexible circuit assemblies are contemplated that lack one or more of the joining members illustrated in FIG. 3.

Figure 5:
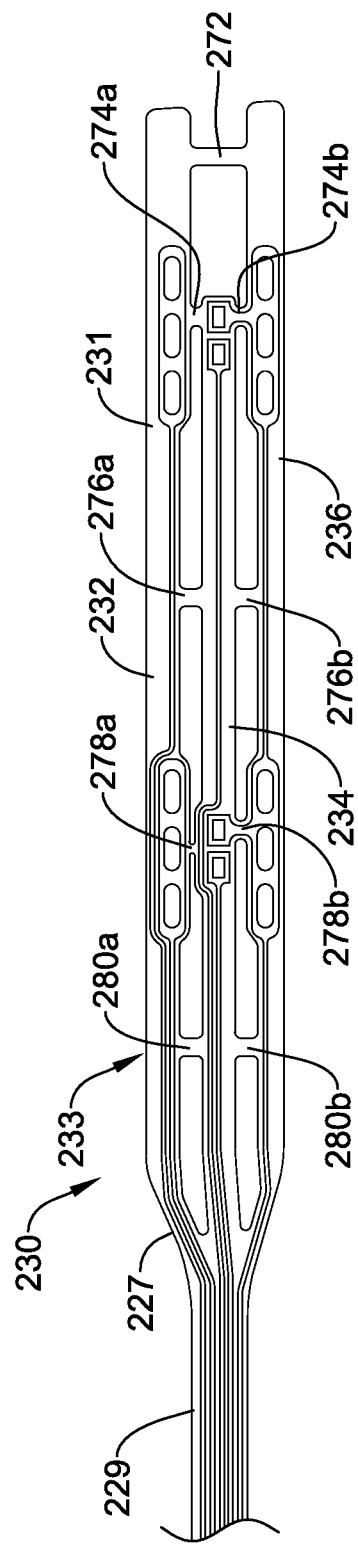
FIG. 5 is a side view of another example flexible circuit assembly.

FIG. 5 illustrates another example flexible circuit assembly 230 that may be similar in form and function to other assemblies disclosed herein. Assembly 230 may include substrate 233 having proximal region 229, distal region 231, and tapered region 227 disposed therebetween. In this example, first electrode strip 232, sensor strip 234, and second electrode strip 236 are interconnected by one or more joining members such as joining members 272/276a/276b/278a/278b/280a/280b. Furthermore, in this example the longitudinal axis of proximal region 229 of substrate and distal region 231 of substrate 233 are substantially aligned. In other words, flexible circuit assemblies are contemplated where distal region 231 of substrate 233 is not angled or slanted relative to proximal region 229 of substrate.

Figure 6:
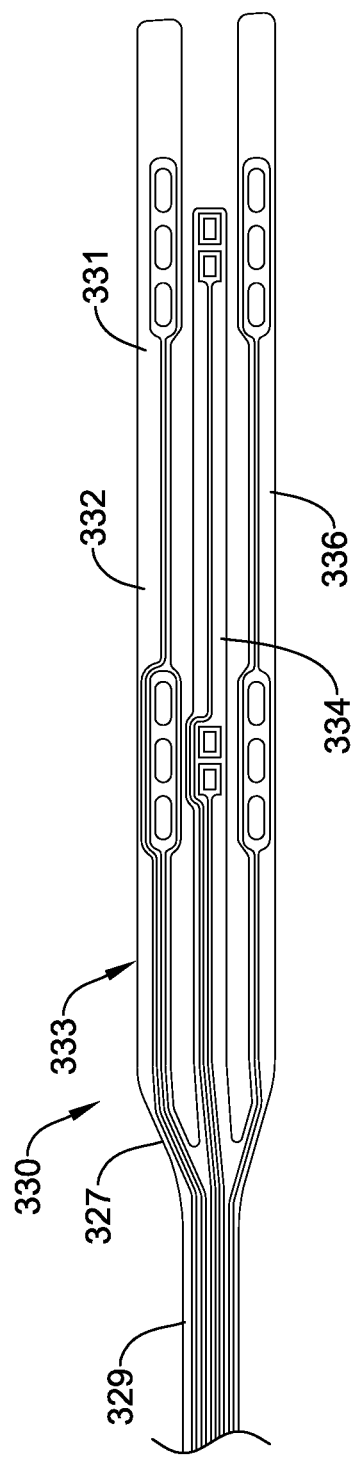
FIG. 6 is a side view of another example flexible circuit assembly.

FIG. 6 illustrates another example flexible circuit assembly 330 that may be similar in form and function to other assemblies disclosed herein. Assembly 330 may include substrate 333 having proximal region 329, distal region 331, and tapered region 327 disposed therebetween. In this example, first electrode strip 332, sensor strip 334, and second electrode strip 336 are substantially free from connection along their lengths. This example illustrates that assemblies are contemplated that both lack one or more joining member and that are not slanted or angled.

Figure 7:
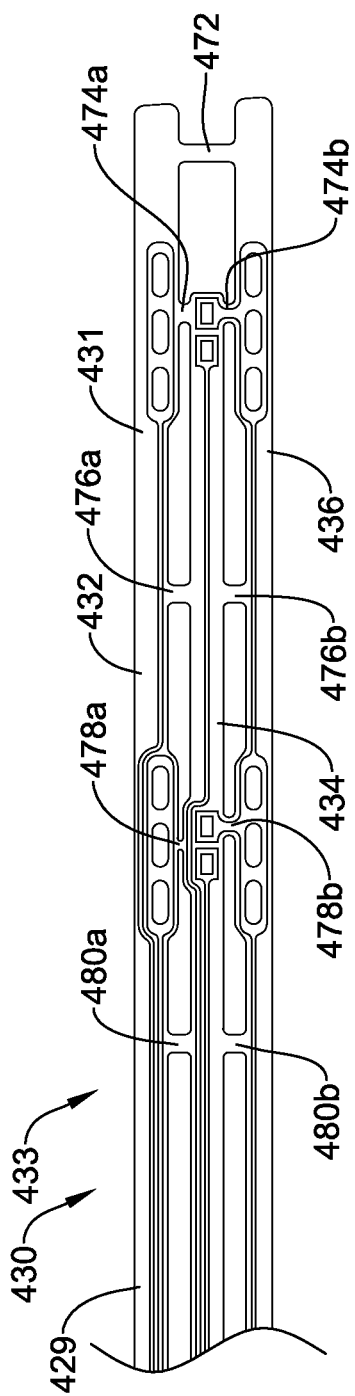
FIG. 7 is a side view of another example flexible circuit assembly.

FIG. 7 illustrates another example flexible circuit assembly 430 that may be similar in form and function to other assemblies disclosed herein. Assembly 430 may include substrate 433 having proximal region 429 and distal region 431. In this example, first electrode strip 432, sensor strip 434, and second electrode strip 436 are interconnected by one or more joining members such as joining members 472/476a/476b/478a/478b/480a/480b. In this example, substrate 433 lacks a tapered region. Accordingly, proximal region 429 of substrate 433 and distal region 431 of substrate 433 have substantially the same width. This may help to further reduce the amount of force that may be exposed to assembly 430 when, for example, withdrawing assembly 430 into guide catheter 14.

Figure 8:
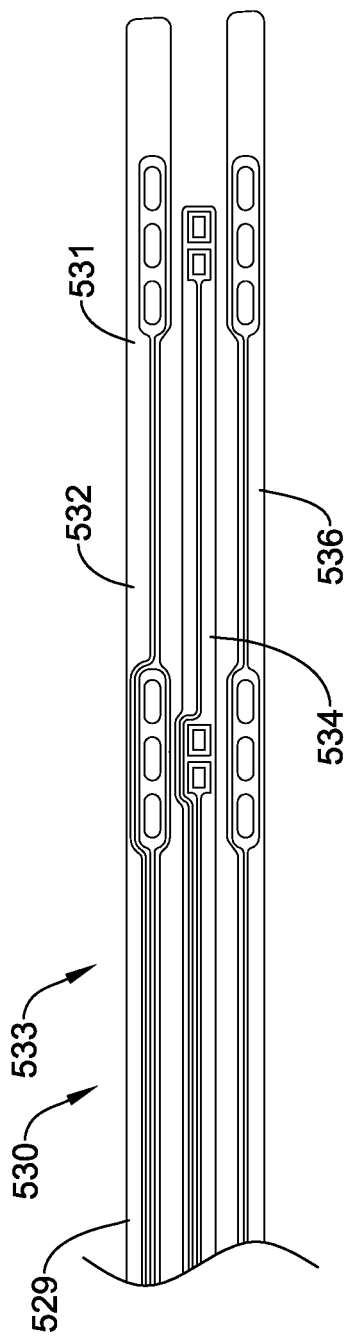
FIG. 8 is a side view of another example flexible circuit assembly.

FIG. 8 illustrates another example flexible circuit assembly 530 that may be similar in form and function to other assemblies disclosed herein. Assembly 530 may include substrate 533 having proximal region 529 and distal region 531. In this example, first electrode strip 532, sensor strip 534, and second electrode strip 536 are substantially free from connection along their lengths. This example illustrates that assemblies are contemplated that lack one or more joining member, that are not slanted or angled, and that have a substantially constant width.

Figure 9:
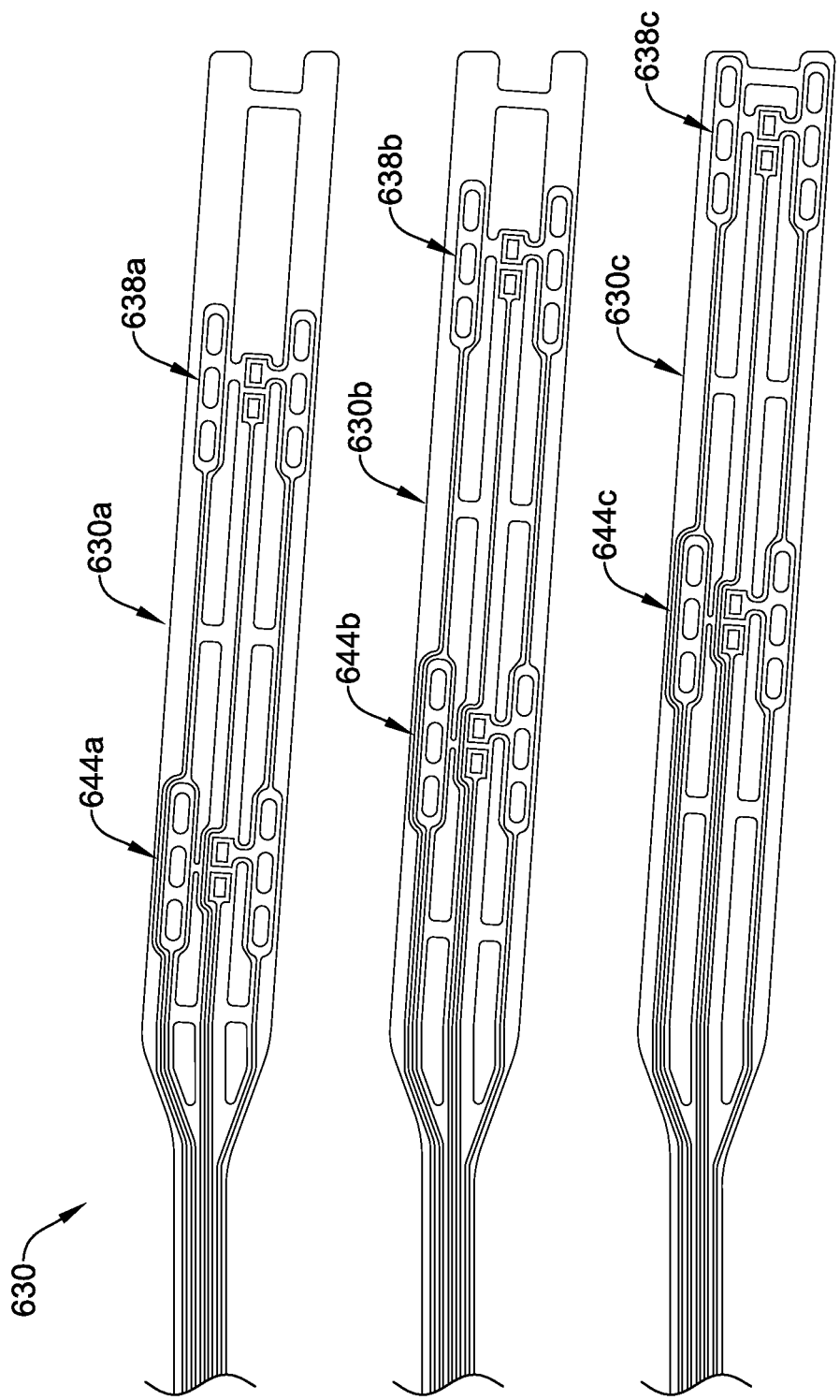
FIG. 9 is a side view of another example flexible circuit assembly.
Figure 10:
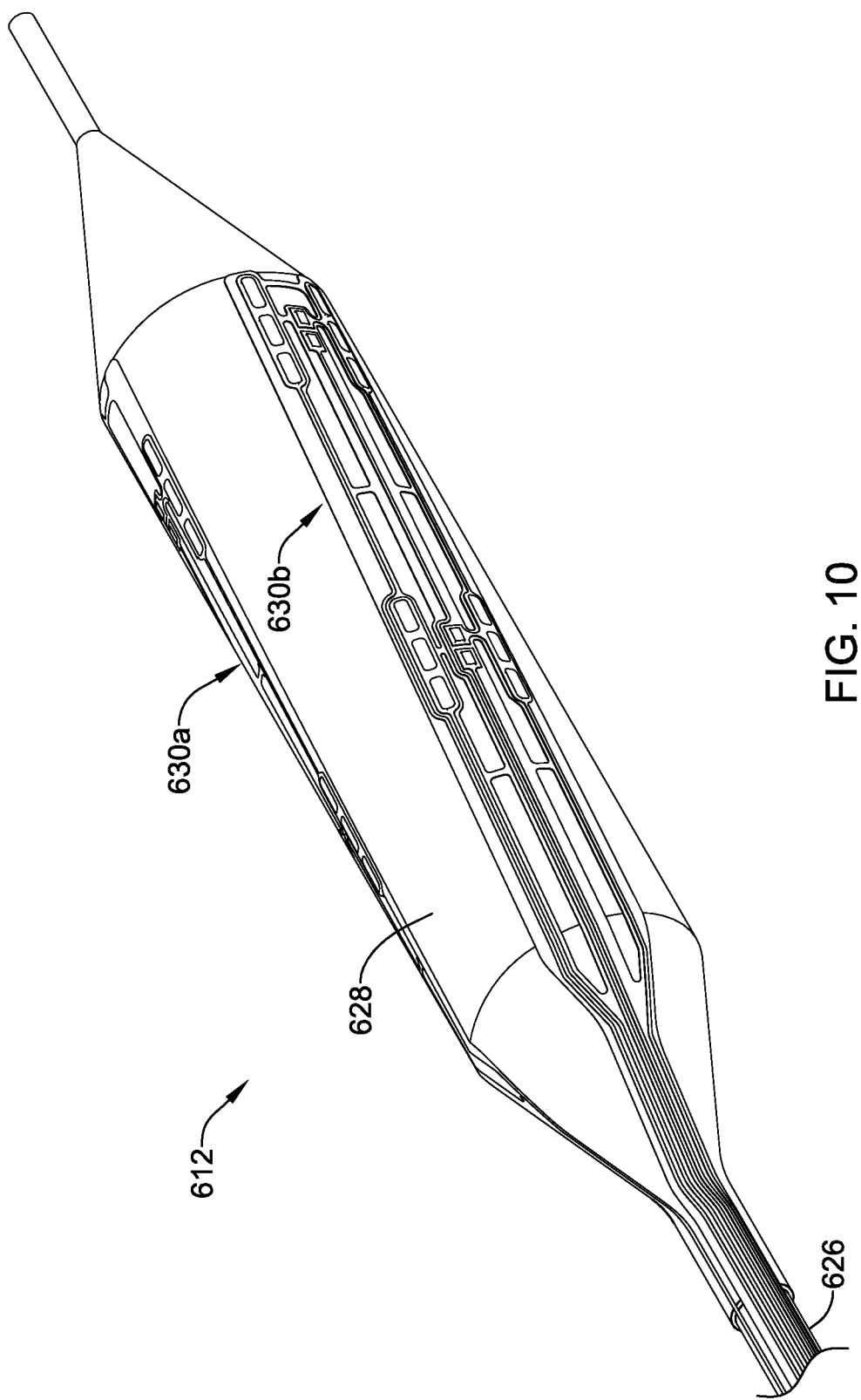
FIG. 10 is a perspective view of an example medical device including the flexible circuit assembly shown in FIG. 9.

FIG. 9 illustrates another example flexible circuit assembly 630 that may be similar in form and function to other assemblies disclosed herein. In this example, assembly 630 includes a collection of individual flexible circuit assemblies 630a/630b/630c. Each of the assemblies may be the same or they may differ. For example, in FIG. 9 the relative position of the distal electrode assemblies or pads 636a/636b/636c and/or the relative position of the proximal electrode assemblies or pads 644a/644b/644c may differ along the length of each assembly 630a/630b/630c. FIG. 10 illustrates a portion of an example medical device 612 that may be similar to other devices disclosed herein. Device 612 may include catheter shaft 626 and expandable member/balloon 628. The components of flexible circuit assembly 630 (as shown in FIG. 9) may be coupled to balloon 628. In this figure, assembly 630a and assembly 630b can be seen.

Figure 11:
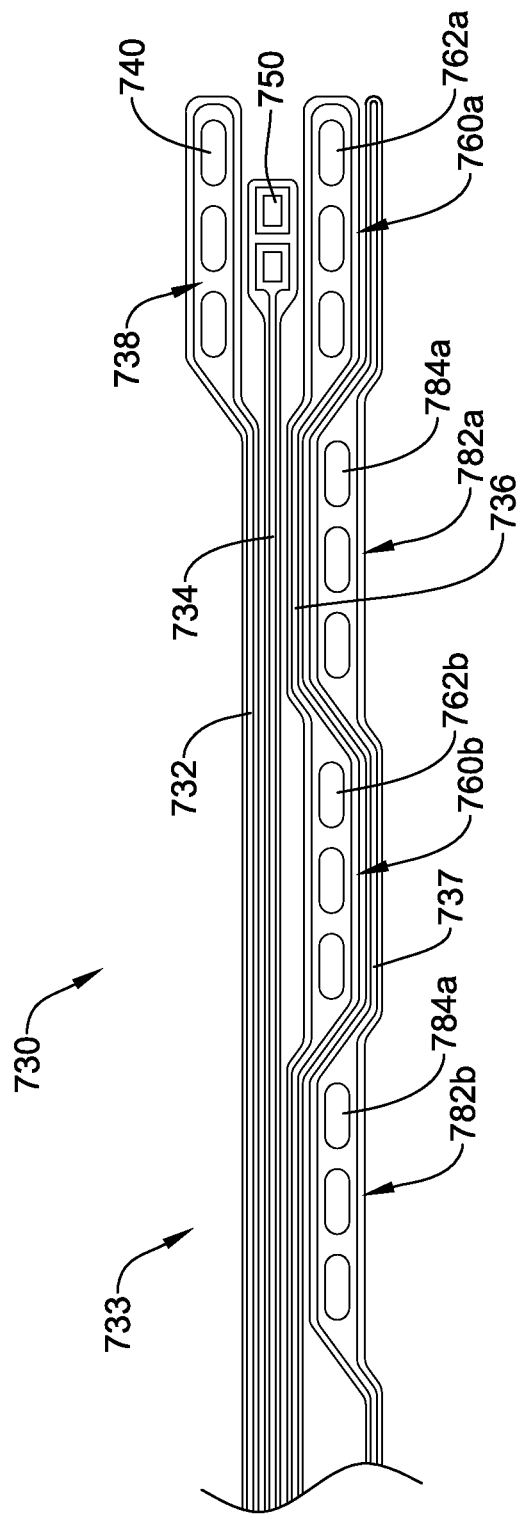
FIG. 11 is a side view of another example flexible circuit assembly.

FIG. 11 illustrates another example flexible circuit assembly 730 that may be similar in form and function to other assemblies disclosed herein. Assembly 730 may include substrate 733 having a plurality of sections or strips such as first electrode strip 732, sensor strip 734, second electrode strip 736, and a third electrode strip 737. First electrode strip 732 may include electrode assembly or pad 738 including one or more electrodes 740. Sensor strip 734 may include one or more sensors 750. Second electrode strip 736 may include a distal electrode assembly or pad 760a including one or more electrodes 762a and a proximal electrode assembly or pad 760b including one or more electrodes 762b. Third electrode strip 737 may include a distal electrode assembly or pad 782a including one or more electrodes 784a and a proximal electrode assembly or pad 782b including one or more electrodes 784b.

In the example shown in FIG. 11, strips 732/734/736/737 may be described as being nested. Such a configuration may allow for assembly 730 to have a relatively compact shape while still having a relatively large number of electrodes. In some embodiments, strips 732/734/737 may have a width in the range of about 0.010-0.030 inches or less, or about 0.015-0.025 inches or less, or about 0.02 inches or less. Pads 738/760a/760b/782a/782b may have an increased width relative to the remaining portions of strips 732/734/737. For example, pads 738/760a/760b/782a/782b may have a width in the range of about 0.015-0.035 inches, or about 0.02-0.03 inches, or about 0.023-0.025 inches. Adjacent to sensor(s) 750, strip 734 may have a width in the range of about 0.015-0.040 inches, or about 0.02-0.035 inches, or about 0.03 inches. These are just examples. Other dimensions are contemplated. Such dimensions may not only allow for assembly 730 to be utilized with a balloon (e.g., as shown in FIG. 12), they may also allow assembly 730 to be sufficiently compact so that assembly 730 may be attached to or otherwise used on a basket or strut-like structure including relatively "thin" struts (e.g., on the order of about 0.05-0.08 inches or so, or about 0.066 inches or so).

Figure 12:
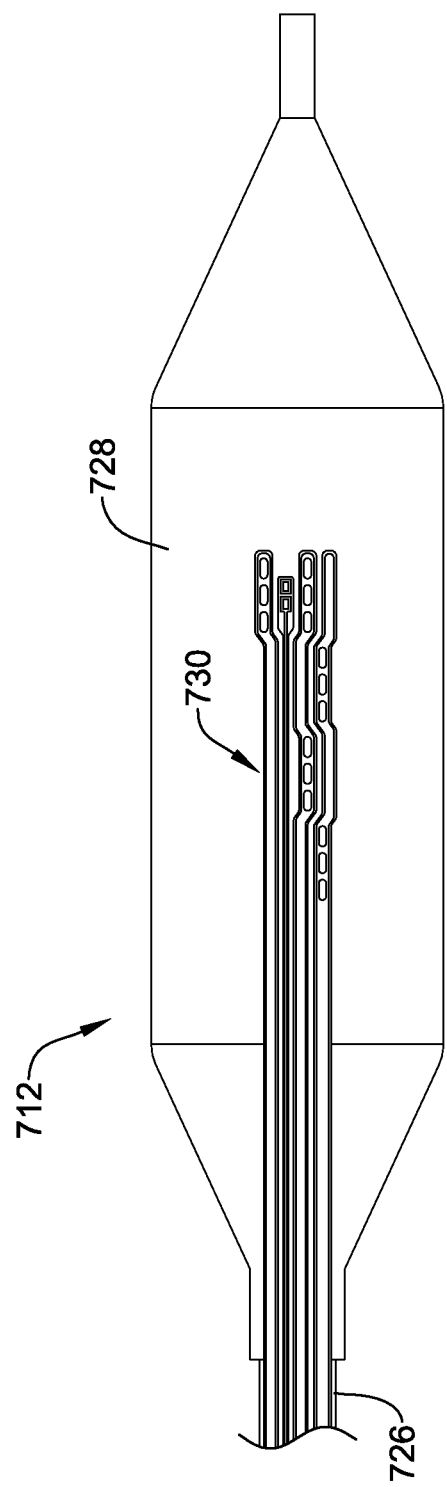
FIG. 12 is a side view of an example medical device including the flexible circuit assembly shown in FIG. 11.

FIG. 12 illustrates a portion of an example medical device 712 that may be similar to other devices disclosed herein. Device 712 may include catheter shaft 726 and expandable member/balloon 728. Flexible circuit assembly 730 may be coupled to balloon 628. As indicated above, assembly 730 may be used with balloon 728 or with other structures such as baskets, struts, or the like.

Figure 13:
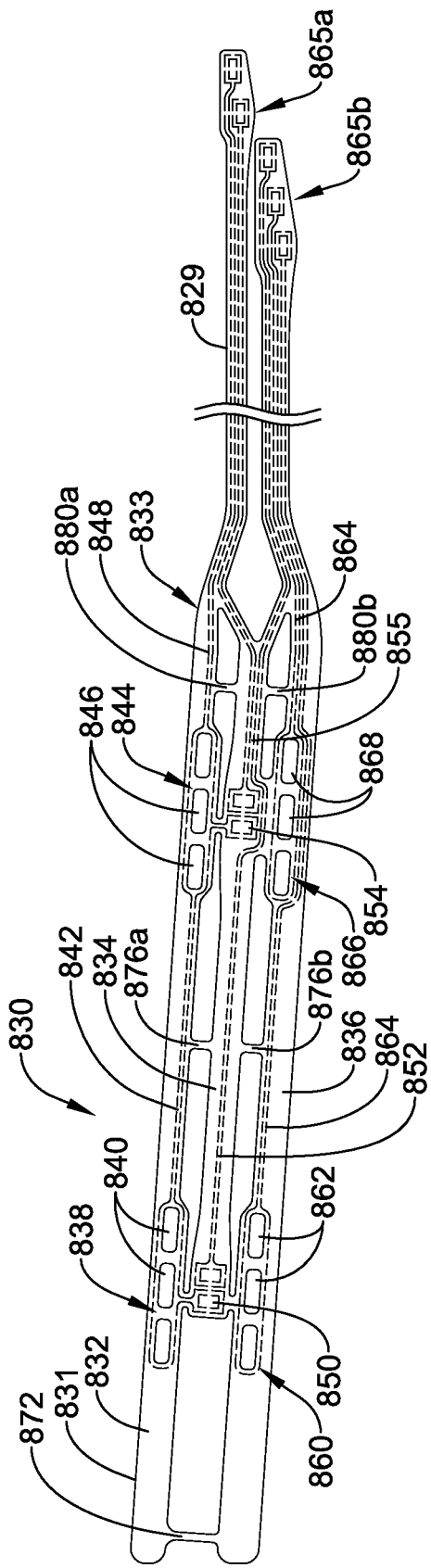
FIG. 13 is a side view of another example flexible circuit assembly.
Figure 14:
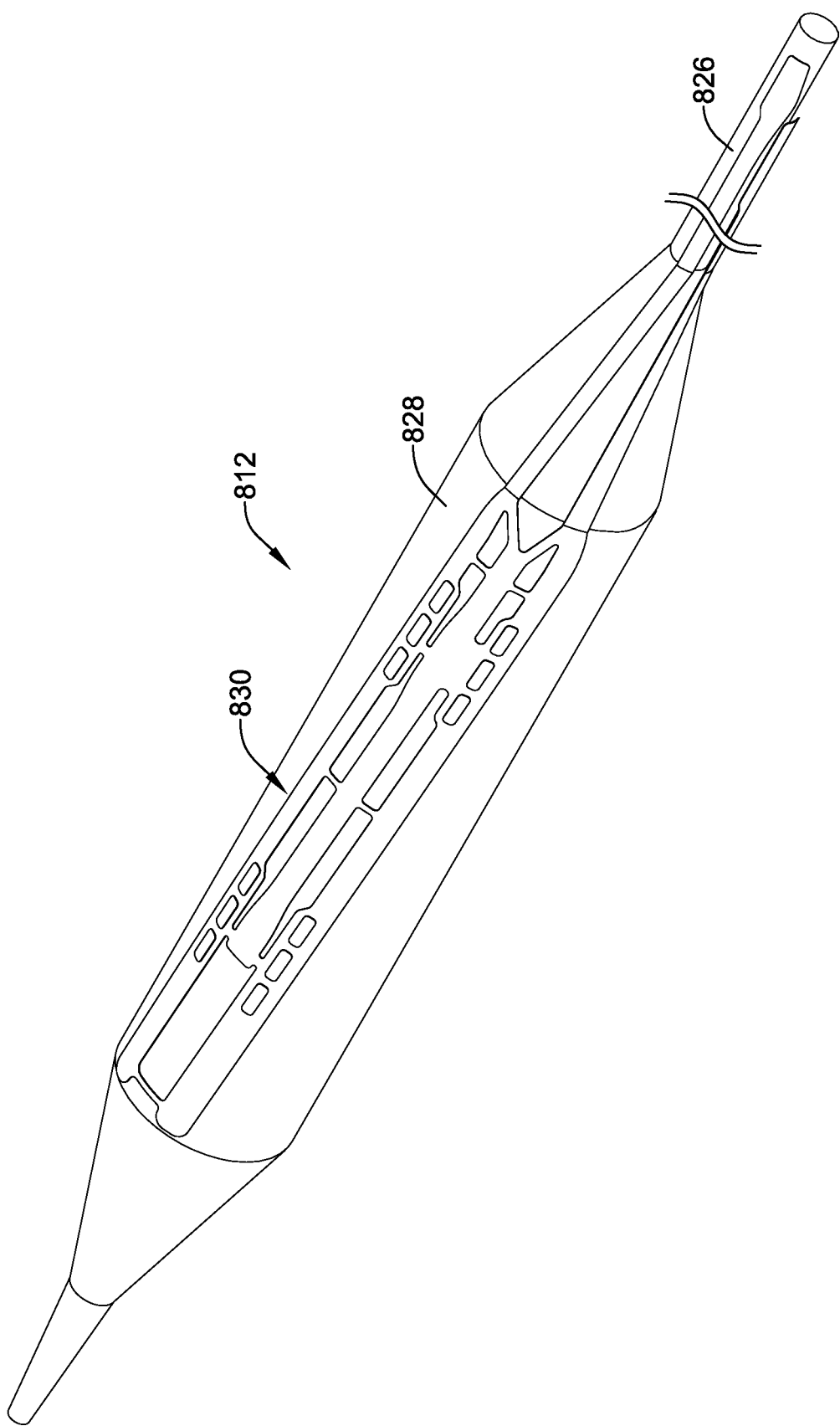
FIG. 14 is a perspective view of the example flexible circuit assembly shown in FIG. 13 coupled to a balloon.

FIG. 13 is a side view of flexible circuit assembly 830 that may be similar in form and function to other assemblies disclosed herein. FIG. 14 illustrates medical device 812 including shaft 826, balloon 828 coupled to shaft 826, and assembly 830 coupled to balloon 828. Device 812 may be similar to other devices disclosed herein.

As shown in FIG. 13, assembly 830 may include substrate 833 having proximal region 829 and distal region 831. Substrate 833 may include first electrode strip 832, sensor strip 834, and second electrode strip 836. First electrode strip 832 may include distal electrode assembly or pad 838 having one or more electrodes 840. One or more leads 842 may be coupled to electrodes 840 and extend proximally therefrom. In some embodiments, first electrode strip 832 may also include one or more additional electrode assemblies such as proximal electrode assembly or pad 844 having one or more electrodes 846. One or more leads 848 may be coupled to electrodes 846 and extend proximally therefrom. Leads 842/848, which are shown schematically, may be electrically coupled to control unit 18 so that electrodes 840/846 may be suitably energized.

Sensor strip 834 may include one or more sensors such as a sensor or sensors 850. In the drawing, two sensors 850 are shown. However, in other embodiments only one or more than two sensors may be utilized. In at least some embodiments, sensor 850 is a temperature sensor that may be disposed along a top (outward facing when in use) or bottom surface (inward facing that may be, for example, disposed along an outer surface of a balloon when in use) of sensor strip 834. For example, sensor(s) 850 may include a thermistor, thermocouple, or the like. In other embodiments, sensor(s) 850 may include another type of sensor such as a pressure sensor, force sensor, or the like. One or more leads 852 may be coupled to sensor(s) 850 and extend proximally therefrom. In some embodiments, sensor strip 834 may also include one or more additional sensors such as sensor or sensors 854. One or more leads 856 may be coupled to sensor(s) 854 and extend proximally therefrom. Leads 852/856, which are shown schematically, may be electrically coupled to control unit 18 so that sensors 850/854 may be suitably energized. In at least some embodiments, leads 852/856 may be omitted and, instead, sensor(s) 850 may be electrically coupled to leads 842/848 and/or other leads disposed along substrate 833.

Second electrode strip 836 may include a distal electrode assembly or pad 860 having one or more electrodes 862. One or more leads 864 may be coupled to electrodes 862 and extend proximally therefrom. In some embodiments, second electrode strip 836 may also include one or more additional electrode assemblies such as a proximal electrode assembly or pad 866 having one or more electrodes 868. One or more leads 870 may be coupled to electrodes 868 and extend proximally therefrom. Leads 864/870, which are shown schematically, may be electrically coupled to control unit 18 so that electrodes 862/868 may be suitably energized.

First electrode strip 832 and second electrode strip 836 may be interconnected at a first location by a joining member 872. Joining member 872 may take the form of a portion or section of substrate 833 that extends between strips 832/836. In other embodiments joining member 872 may be a separate members that is attached to both of strips 832/836. Strips 832/834/836 may be interconnected at one or more locations by one or more joining members such as joining members 876a/876b/880a/880b. The precise location of the various joining members along strips 832/834/836 may vary. Fewer or more joining members may be utilized without departing from the spirit of the disclosure.

Substrate 833 may also include one or more connector regions such as connector regions 856a/856b. Regions 865a/856b may include one or more connectors that allow the various leads to be electrically coupled to a conductive member such as a wire. The precise form of regions 865a/865b may vary. A number of arrangements and/or configurations are contemplated.

Figure 15:
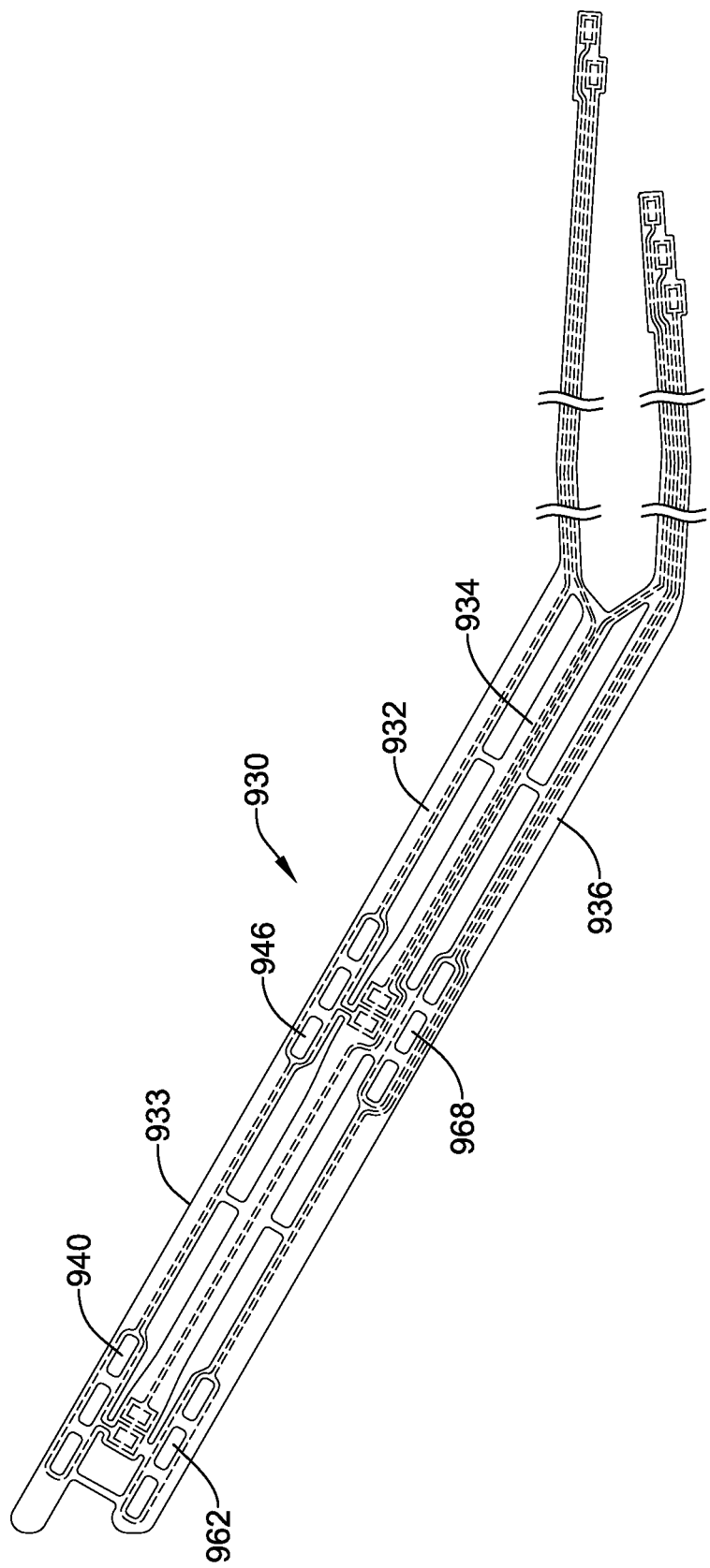
FIG. 15 is a side view of another example flexible circuit assembly.
Figure 16:
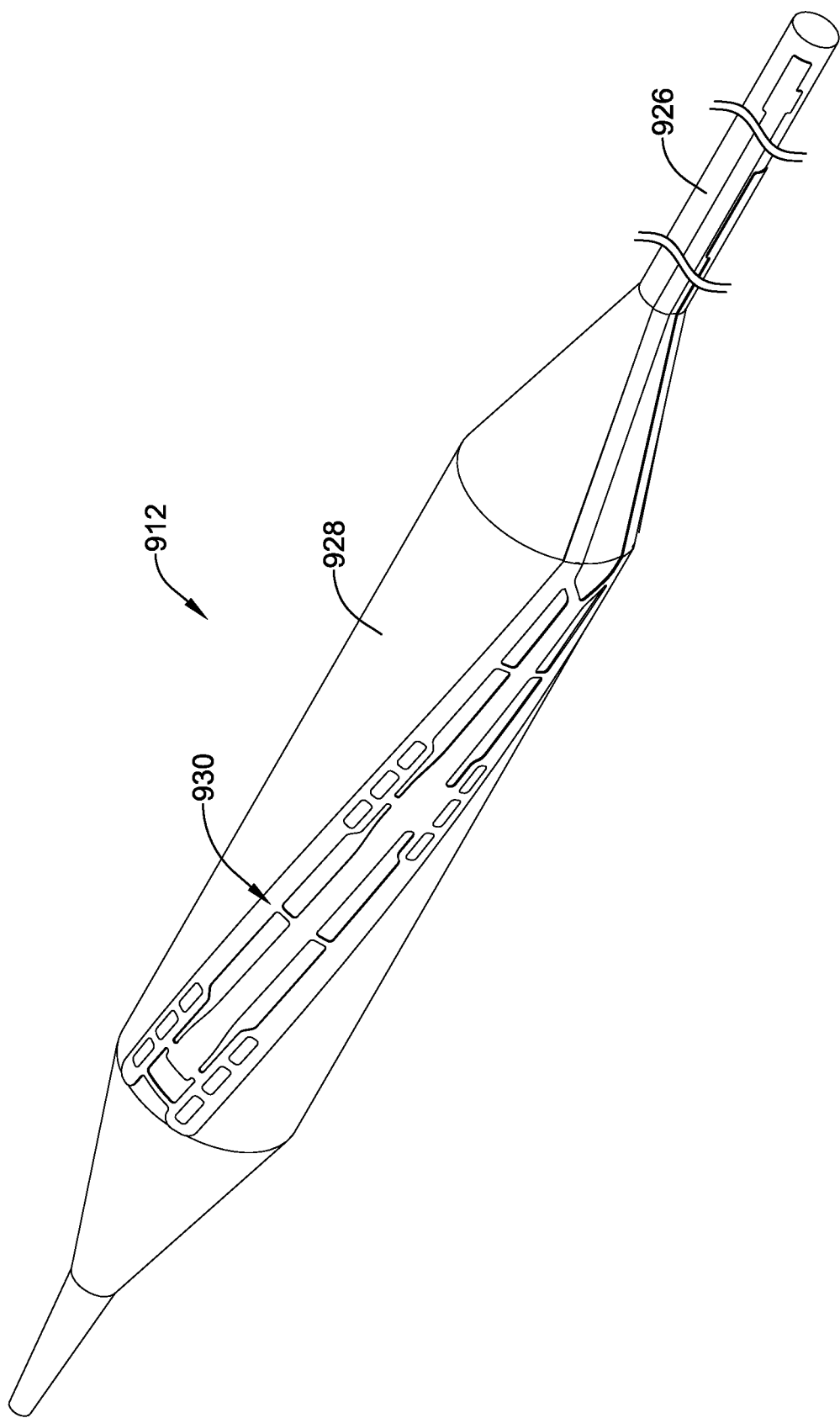
FIG. 16 is a perspective view of the example flexible circuit assembly shown in FIG. 15 coupled to a balloon.

FIG. 15 illustrates another example flexible circuit assembly 930 that may be similar in form and function to other flexible circuit assemblies disclosed herein. FIG. 16 illustrates medical device 912 including shaft 926, balloon 928 coupled to shaft 926, and flexible circuit assembly 930 coupled to balloon 928. Device 912 may be similar to other devices disclosed herein. Referring now to FIG. 15, flexible circuit assembly 930 may include substrate 933 and strips 932/934/936. A number of electrodes such as electrodes 940/946/962/968 may be disposed along strips 932/934/936.

Figure 17:
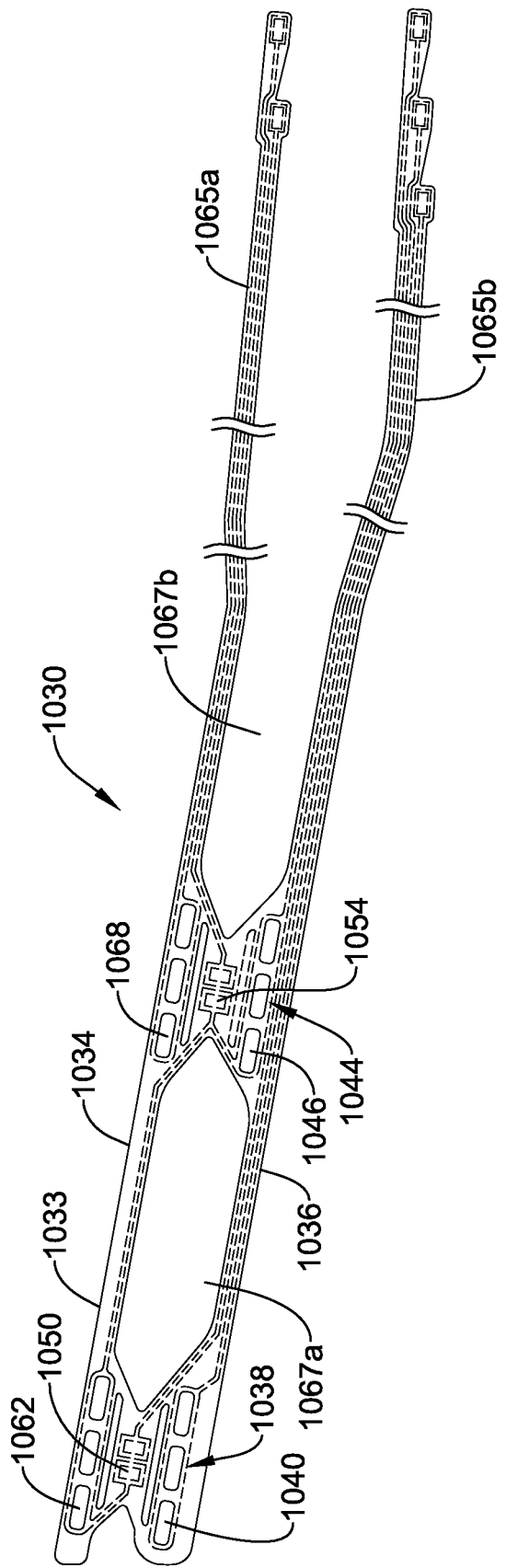
FIG. 17 is a side view of another example flexible circuit assembly.
Figure 18:
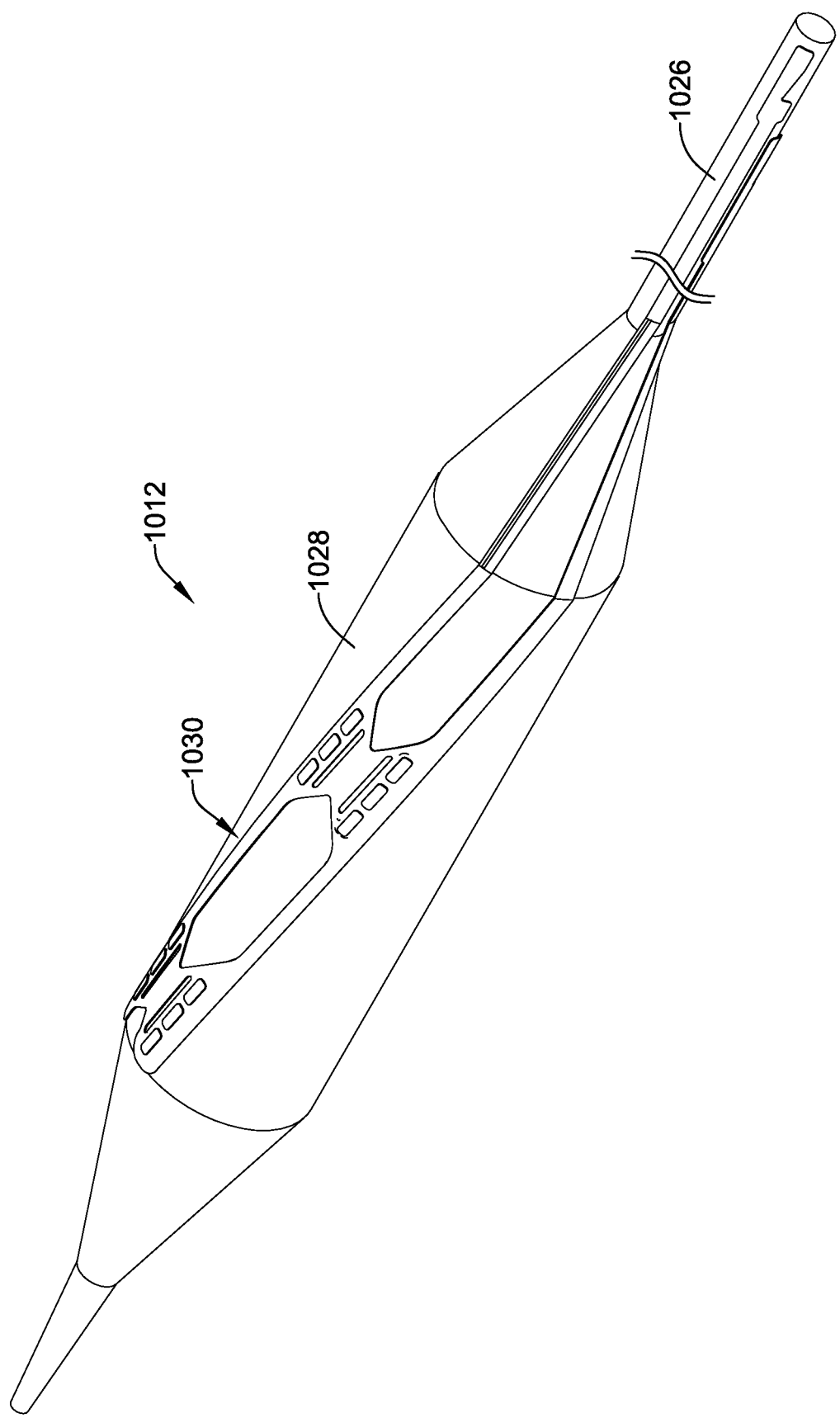
FIG. 18 is a perspective view of the example flexible circuit assembly shown in FIG. 17 coupled to a balloon.

FIG. 17 illustrates another example flexible circuit assembly 1030 that may be similar in form and function to other flexible circuit assemblies disclosed herein. FIG. 18 illustrates medical device 1012 including shaft 1026, balloon 1028 coupled to shaft 1026, and flexible circuit assembly 1030 coupled to balloon 1028. Device 1012 may be similar to other devices disclosed herein.

Referring now to FIG. 17, flexible circuit assembly 1030 may include substrate 1033. Substrate may include a first strip 1034 and a second strip 1036. A first electrode pad 1038 may be disposed adjacent to a distal end of strips 1034/1036. Pad 1038 may include electrodes 1040/1062 and sensor 1050. A second electrode pad 1044 may be disposed proximal of pad 1038. Pad 1044 may include electrodes 1046/1068 and sensor 1054. Flexible circuit assembly 1030 may include a first cutout region 1067a and a second cutout region 1067b. Cutout regions 1067a/1067b may essentially allow for assembly 1030 to have a greater flexibility and also allow for a central "sensor strip" (e.g., like those seen in other flexible circuit assemblies disclosed herein) to be omitted. Cutout region 1067b may define a "X" or "X-like" shape along a proximal section of assembly 1030. It can be appreciated that a number of different shapes and/or configurations are contemplated for cutout regions 1067a/1067b.

Tails or tail regions 1065a/1065b may extend proximally along or otherwise from cutout region 1067b. Tails 1065a/1065b may be disposed along a cone region of balloon 1028 when mounting assembly 1030 to balloon 1028. In some embodiments, tails 1065a/1065b may extend to a position along shaft 1026. In other embodiments, tails 1065a/1065b may extend along essentially the full length of shaft 1026 and be coupled to control unit 18.

From the various flexible circuit assemblies disclosed herein it can be appreciated that a number of structural variations are contemplated. In addition to what is disclosed herein, a number of further variations are contemplated that may be applicable to any of the flexible circuit assemblies disclosed herein. For simplicity purposes, the following disclosure refers to flexible circuit assembly 1030. However, it can be appreciated that the following disclosure may also be applied to any of the other flexible circuit assemblies disclosed herein, as appropriate.

Flexible circuit assembly 1030, much like assembly 30, may have a canted or angled configuration. In other words, at least a portion (e.g., a distal portion) of flexible circuit assembly 1030 may be canted relative to another portion (e.g., a proximal portion). Canting may be desirable for a number of reasons. For example, canting may help to streamline the edges of flexible circuit assembly 1030 so as to reduce the number of catch points that might otherwise "catch" when retracting assembly 1030 (e.g., a device including assembly 1030) into a sheath or guide catheter. In at least some embodiments, the canting of assembly 1030 may allow assembly 1030 to function much like a rail when retracting assembly 1030 (e.g., a device including assembly 1030) into a sheath or guide catheter. In addition, canting may help to promote rewrapping of a balloon (e.g., when assembly 1030 is secured to a balloon). The amount of canting (e.g., the canting angle) may vary. For example, assembly 1030 may be canted about 45 degrees or less, or about 5-30 degree, or about 10-15 degree. These are just examples.

As indicated herein, assembly 1030 may include cutout regions 1067a/1067b and may generally be configured to include strips 1034/1038. This configuration (and similar configurations disclosed herein) may allow for less material to be utilized for substrate 1033. The smaller amount of material may desirably impact flexibility and/or balloon rewrapping. For example, less material may provide fewer obstacles to balloon rewrapping and/or folding. It may also be desirable to further reduce the thickness of substrate 1033. This may allow for the overall profile of assembly 1030 to be reduced. As such, smaller profile devices may be used in conjunction with assembly 1030 (e.g., a 6F guide catheter may be used to deliver assembly 1030 and/or devices using assembly 1030).

Reducing the thickness of substrate 1033 may include laser ablation of the substrate, which may remove portions of the thickness of substrate 1033. For example, substrate 1033 may include a number of layers including an outer layer, an electrode layer, and an inner layer. The inner layer may also be termed the "cover layer". In at least some embodiments, the cover layer may be ablated to remove a portion thereof. For example, 50% or more of the cover layer may be removed to reduce the thickness of assembly 1030, or about 60% or more may be removed, or about 70% or more may be removed. In some embodiments, the cover layer may be completely removed altogether. In addition to removing material from substrate 1033, material changes may also be utilized. Such changes could also desirably impact the profile of assembly 1030. For example, in some embodiments materials such as polyethylene terephthalate or other suitable materials may be used.

As shown, assembly 1030 may include a plurality of electrode pads such as pads 1038/1044. While two pads (as shown) may be suitable, more or fewer pads may be utilized. For example, assembly 1030 may include about 1-10 pads, or about 1-3 pads, or about 1-2 pad. In addition, the spacing of pads on adjacent flexible circuit assemblies may also be varied in order to achieve the desired therapy. For example, it may be desirable for various pads on adjacent flexible circuit assemblies to be circumferentially and/or axial spaced. It can be appreciated that circumferential spacing may be varied from the pads on adjacent flexible circuit assemblies being circumferentially overlapped (which may result in an ablation pattern that is continuous) to the pads on adjacent flexible circuit assemblies being circumferentially spaced (which may result in an ablation pattern with circumferential spacing). In some embodiments, the edges of pads on circumferentially adjacent flexible circuit assemblies may be about 1.7-2.5 mm apart, or about 1.85-2.3 mm apart. In some embodiments, the target treatment temperature and/or the control algorithm may be altered so that even greater spacing may be utilized (e.g., up to about 4 mm or more). Axial spacing may also vary from configurations where there is axial overlap of pads on adjacent flexible circuit assemblies to configurations where there is axial spacing of pads on adjacent flexible circuit assemblies.

In general, the circumferential and/or axial spacing of pads 1038/1044 and/or the electrodes thereon can impact the therapy delivery by a given assembly. For example, circumferential overlap may allow for a therapy to include a complete circumferential lesion. This may be desirable in some interventions, for example such as renal nerve ablation, where a complete circumferential ablation may provide a greater likelihood that one or more nerves are sufficiently modulated and/or ablated. Circumferential overlap may also allow for greater treatment depths (e.g., 1-4 mm or more). Furthermore, greater circumferential coverage may also allow for less energy or power utilization, more consistent ablation temperatures, increased ablation areas (and/or volumes), or the like.

The number of flexible circuit assemblies utilized per device may also vary. For example, a given device may include 1-20 flexible circuit assemblies, or about 1-10 flexible circuit assemblies, or about 1-3 flexible circuit assemblies. These are just examples.

Variations are also contemplated for balloon 1028 (and/or other balloon disclosed herein). For example, material variations are contemplated including the use of polyethylene terephthalate. The use of polyethylene terephthalate may allow for the construction of balloons with a reduced wall thickness (relative to traditional balloons) while still maintaining sufficient strength. In addition, materials like polyethylene terephthalate have a glass transition temperature above what may be used for the treatment temperature (e.g., $T_g$ may be greater than 70° C.). Because of this, balloon 1028 may be more likely to resist adverse reactions to thermal conditions (e.g., softening, melting, thermal breakdown, etc.). Other variations may include variations in the length of balloon 1028 (e.g., the length of the "body" of balloon 1028). In some embodiments, the length may be in the range of about 10-40 mm, or about 20-30 mm, or about 25 mm. In addition, the angle of "cones" of balloon 1028 (e.g., the regions of the balloon flanking the balloon body and having a generally conical shape) may vary. For example, the cones of balloon 1028 could be oriented at an angle of about 5-45 degrees, or about 10-30 degrees, or about 15-20 degrees. These are just examples. Other variations are contemplated.

The materials that can be used for the various components of device 12 (and/or other devices disclosed herein) may include those commonly associated with medical devices. For simplicity purposes, the following discussion makes reference to device 12 and/or the components thereof. However, this is not intended to limit the devices and methods described herein, as the discussion may be applied to any of the other similar devices disclosed herein.

Device 12 and/or other components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of device 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 12 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of device 12 to achieve the same result.

In some embodiments, a degree of Magnetic Resonance Imaging (MRI) compatibility is imparted into device. For example, device 12, or portions thereof, may be made of a material that does not substantially distort the image and create substantial artifacts (i.e., gaps in the image). Certain ferromagnetic materials, for example, may not be suitable because they may create artifacts in an MRI image. Device 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

U.S. patent application Ser. No. 13/750,879 filed on Jan. 25, 2013 is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device for sympathetic nerve modulation, comprising:
   a catheter shaft having a distal section;
   a balloon comprising a cylindrical balloon body coupled to the distal section;
   a flexible circuit assembly, the flexible circuit assembly including a polymer substrate with a proximal region coupled to the catheter shaft and a distal region coupled to the balloon;
   wherein the distal region of the polymer substrate includes an elongate first electrode strip, an elongate second electrode strip, and an elongate sensor strip disposed between and spaced apart from the first electrode strip and the second electrode strip;
   wherein a plurality of electrodes is disposed over the first electrode strip;
   wherein a plurality of electrodes is disposed over the second electrode strip;
   wherein a plurality of sensors is disposed over the sensor strip;
   wherein the first electrode strip is connected to the sensor strip by a first plurality of spaced apart joining members that are formed from the polymer substrate material, wherein the first electrode strip and the sensor strip are distinct from one another except where connected to one another by the joining members, wherein the second electrode strip is connected to the sensor strip by a second plurality of spaced apart joining members that are formed from the polymer substrate material, wherein the second electrode strip and the sensor strip are distinct from one another, except where connected to one another by the joining members; and
   wherein a plurality of bipolar electrode pairs is defined by the plurality of electrodes disposed over the first electrode strip and the plurality of electrodes disposed over the second electrode strip.

2. The medical device of claim 1, wherein the proximal region of the polymer substrate and the distal region of the polymer substrate have substantially the same width.

3. The medical device of claim 1, wherein the proximal region of the polymer substrate has a first width, and wherein the distal region of the polymer substrate has a second width greater than the first width.

4. The medical device of claim 1, wherein the distal region of the polymer substrate is slanted relative to a longitudinal axis of the proximal region of the polymer substrate.

5. The medical device of claim 1, wherein the distal region of the polymer substrate is attached to an outer surface of the balloon.

6. A method for modulating sympathetic nerves, the method comprising:
   advancing the medical device for sympathetic nerve modulation of claim 1 through a blood vessel to a position within the body;
   expanding the balloon; and
   activating at least one pair of the plurality of bipolar electrode pairs.

7. The medical device of claim 1, wherein the first elongate electrode strip, the second elongate electrode strip, and the elongate sensor strip each extend longitudinally along a length of the cylindrical balloon body.

8. The medical device of claim 7, wherein the first elongate electrode strip, the second elongate electrode strip, and the elongate sensor strip are canted relative to a longitudinal axis of the cylindrical balloon body.

9. The medical device of claim 7, wherein the first elongate electrode strip, the second elongate electrode strip, and the elongate sensor strip are parallel to one another.

10. The medical device of claim 7, wherein the first elongate electrode strip and the second elongate electrode strip each comprises a plurality of longitudinally spaced apart groups of electrodes.

11. A medical device, comprising:
    a catheter shaft having a distal section;
    a balloon comprising a cylindrical balloon body coupled to the distal section;
    a flexible circuit assembly including a polymer substrate with a proximal region and a distal region, the flexible circuit assembly coupled to the balloon;
    wherein the distal region of the polymer substrate includes an elongate first electrode strip, an elongate second electrode strip, and an elongate sensor strip disposed between and spaced apart from the first electrode strip and the second electrode strip;
    wherein a plurality of electrodes is disposed over the first electrode strip;
    wherein a plurality of electrodes is disposed over the second electrode strip;
    wherein a plurality of sensors is disposed over the sensor strip;
    wherein the first electrode strip is connected to the sensor strip by a first plurality of spaced apart joining members that are formed from the polymer substrate material, wherein the first electrode strip and the sensor strip are distinct from one another except where connected to one another by the joining members, wherein the second electrode strip is connected to the sensor strip by a second plurality of spaced apart joining members that are formed from the polymer substrate material, wherein the second electrode strip and the sensor strip are distinct from one another, except where connected to one another by the joining members; and
    wherein a plurality of bipolar electrode pairs is defined by the plurality of electrodes disposed over the first electrode strip and the plurality of electrodes disposed over the second electrode strip.

12. The medical device of claim 11, wherein a proximal region of the polymer substrate and a distal region of the polymer substrate have substantially the same width.

13. The medical device of claim 11, wherein a proximal region of the polymer substrate has a first width, and wherein a distal region of the polymer substrate has a second width greater than the first width.

14. The medical device of claim 11, wherein the first elongate electrode strip, the second elongate electrode strip, and the elongate sensor strip each extend longitudinally along a length of the cylindrical balloon body.

15. The medical device of claim 14, wherein the first elongate electrode strip, the second elongate electrode strip, and the elongate sensor strip are canted relative to a longitudinal axis of the cylindrical balloon body.

16. The medical device of claim 14, wherein the first elongate electrode strip, the second elongate electrode strip, and the elongate sensor strip are parallel to one another.

17. The medical device of claim 14, wherein the first elongate electrode strip and the second elongate electrode strip each comprises a plurality of longitudinally spaced apart groups of electrodes.

18. A method for modulating sympathetic nerves, the method comprising:
    advancing the medical device for sympathetic nerve modulation of claim 11 through a blood vessel to a position within the body;
    expanding the balloon; and
    activating at least one pair of the plurality of bipolar electrode pairs.

19. A medical device, comprising:
    a catheter shaft having a distal section;
    a balloon coupled to the distal section;
    a flexible circuit assembly including a polymer substrate with a proximal region and a distal region, the flexible circuit assembly coupled to the balloon;
    wherein the distal region of the polymer substrate includes an elongate first electrode strip, an elongate second electrode strip, and an elongate sensor strip disposed between and spaced apart from the first electrode strip and the second electrode strip;
    wherein a plurality of electrodes is disposed over the first electrode strip;
    wherein a plurality of electrodes is disposed over the second electrode strip;
    wherein a plurality of sensors is disposed over the sensor strip;
    wherein the first electrode strip is connected to the sensor strip by a first plurality of spaced apart joining members that are formed from the polymer substrate material, wherein the first electrode strip and the sensor strip are distinct from one another except where connected to one another by the joining members, wherein the second electrode strip is connected to the sensor strip by a second plurality of spaced apart joining members that are formed from the polymer substrate material, wherein the second electrode strip and the sensor strip are distinct from one another, except where connected to one another by the joining members; and
    wherein a plurality of bipolar electrode pairs is defined by the plurality of electrodes disposed over the first electrode strip and the plurality of electrodes disposed over the second electrode strip.

20. A method for modulating sympathetic nerves, the method comprising:
    advancing the medical device for sympathetic nerve modulation of claim 19 through a blood vessel to a position within the body;
    expanding the balloon; and
    activating at least one pair of the plurality of bipolar electrode pairs.

* * * * *